(12) United States Patent
Cox

(10) Patent No.: US 10,231,882 B2
(45) Date of Patent: Mar. 19, 2019

(54) DEVICE AND METHOD FOR APPLYING PRESSURE TO A MAMMALIAN LIMB

(71) Applicant: Wesley Cox, Fayetteville, AR (US)

(72) Inventor: Wesley Cox, Fayetteville, AR (US)

(73) Assignee: Xtreme Orthopedics LLC, Fayetteville, AR (US)

( * ) Notice: Subject to any disclaimer, the term of this patent is extended or adjusted under 35 U.S.C. 154(b) by 496 days.

(21) Appl. No.: 14/851,135

(22) Filed: Sep. 11, 2015

(65) Prior Publication Data

US 2016/0000612 A1 Jan. 7, 2016

Related U.S. Application Data

(63) Continuation-in-part of application No. 14/022,998, filed on Sep. 10, 2013.

(51) Int. Cl.
*A61F 5/30* (2006.01)
*A61F 13/08* (2006.01)
*A61H 1/00* (2006.01)

(52) U.S. Cl.
CPC .............. *A61F 13/085* (2013.01); *A61F 5/30* (2013.01); *A61H 1/008* (2013.01);
(Continued)

(58) Field of Classification Search
CPC ................... A61H 39/02; A61H 39/04; A61H 2201/1609; A61H 2201/1611; A61H 2201/1614; A61H 2201/1616; A61H 2201/1623; A61H 2201/1626; A61H 2201/1635; A61H 2201/1638;
(Continued)

(56) References Cited

U.S. PATENT DOCUMENTS 1,473,041 A 11/1923 Henderson
2,211,203 A 8/1940 Goldman
(Continued)

FOREIGN PATENT DOCUMENTS

AU 2007309344 5/2008
CA 2667760 5/2008
(Continued)

OTHER PUBLICATIONS

Written Opinion of the International Searching Authority for PCT/US2014/040279 (dated Oct. 1, 2014).
(Continued)

*Primary Examiner* — Michael J Tsai
(74) *Attorney, Agent, or Firm* — Kutak Rock LLP; Bryan P. Stanley

(57) ABSTRACT

A therapeutic pressure band for applying pressure across a muscle or muscle groups on a mammalian limb is described. The band is particularly well suited for treating "shin splints." The band includes a plurality of straps that are connected together via a connecting material. Ends of each of the straps have adjustable fasteners for securing and tightening the band around a limb. The band also possesses a plurality of pressure members (e.g., elongated rubber tubes) that apply separate and discrete areas or points of pressure in a line across a muscle, tendon, bone, or muscle group and generally perpendicular to a longitudinal axis of the limb.

20 Claims, 10 Drawing Sheets

(52) U.S. Cl.
CPC .. *A61H 2201/164* (2013.01); *A61H 2201/165* (2013.01); *A61H 2201/1635* (2013.01); *A61H 2201/1654* (2013.01); *A61H 2201/1697* (2013.01)

(58) Field of Classification Search
CPC ...... A61H 2201/164; A61H 2201/1642; A61H 2201/165; A61F 5/0109; A61F 5/30; A61F 5/32; A61F 5/34; A61F 2013/0028; A61F 5/0102
See application file for complete search history.

(56) References Cited

U.S. PATENT DOCUMENTS

| | | | |
|---|---|---|---|
| 2,594,809 A | 4/1952 | Sanders | |
| 3,074,405 A * | 1/1963 | Duensing | A61F 7/02 |
| | | | 2/22 |
| 3,075,521 A | 1/1963 | Grassl | |
| 3,521,623 A | 7/1970 | Nichols et al. | |
| 3,678,926 A | 7/1972 | Strittmatter | |
| 3,696,810 A | 10/1972 | Gaylord, Jr. | |
| 3,897,777 A | 8/1975 | Morrison | |
| 3,934,583 A * | 1/1976 | Hollingshead | A61F 5/0585 |
| | | | 602/62 |
| 4,066,084 A | 1/1978 | Tillander | |
| D248,872 S | 8/1978 | Thomas | |
| D251,682 S | 4/1979 | Levine | |
| 4,215,687 A | 8/1980 | Shaw | |
| 4,243,028 A * | 1/1981 | Puyana | A61F 13/108 |
| | | | 602/62 |
| 4,334,528 A | 6/1982 | Gauvry | |
| D265,590 S | 7/1982 | Gauvry | |
| 4,370,978 A * | 2/1983 | Palumbo | A61F 13/062 |
| | | | 602/26 |
| 4,378,009 A | 3/1983 | Rowley et al. | |
| 4,474,573 A | 10/1984 | Detty | |
| 4,598,701 A | 7/1986 | Schaefer | |
| 4,628,918 A | 12/1986 | Johnson, Jr. | |
| 4,682,588 A | 7/1987 | Curlee | |
| 4,896,660 A | 1/1990 | Scott | |
| 4,966,136 A | 10/1990 | Bates | |
| 5,063,913 A | 11/1991 | Nyi | |
| 5,152,302 A | 10/1992 | Fareed | |
| 5,154,690 A | 10/1992 | Shiono | |
| D331,801 S | 12/1992 | Shiono | |
| 5,211,623 A | 5/1993 | Sarkozi | |
| 5,295,949 A | 3/1994 | Hathaway | |
| 5,295,951 A | 3/1994 | Fareed | |
| 5,329,941 A | 7/1994 | Bodine, Jr. | |
| 5,372,575 A | 12/1994 | Sebastian | |
| 5,383,844 A | 1/1995 | Munoz et al. | |
| 5,403,268 A | 4/1995 | Clement | |
| 5,423,333 A | 6/1995 | Jensen et al. | |
| 5,445,647 A | 8/1995 | Choy | |
| D369,660 S | 5/1996 | Myoga | |
| 5,591,121 A | 1/1997 | Cantrell | |
| 5,836,904 A * | 11/1998 | Cooper | A61F 5/0109 |
| | | | 602/60 |
| 5,893,871 A | 4/1999 | Tanaka | |
| 5,921,949 A | 7/1999 | Dray | |
| 5,924,120 A | 7/1999 | Razdan et al. | |
| 3,007,508 A | 12/1999 | Reinhardt et al. | |
| D422,362 S | 4/2000 | Ames | |
| 6,077,241 A | 6/2000 | Fareed | |
| 6,077,242 A | 6/2000 | Falk et al. | |
| 6,120,472 A | 9/2000 | Singer, Jr. | |
| 6,149,617 A | 11/2000 | McNally et al. | |
| 6,352,074 B1 | 3/2002 | Okada | |
| 6,361,549 B1 | 3/2002 | Asatourian et al. | |
| D455,213 S | 4/2002 | Weaver, II et al. | |
| 6,398,749 B1 | 6/2002 | Slautterback | |
| 6,402,712 B1 * | 6/2002 | Gauvry | A61F 13/062 |
| | | | 602/26 |
| D462,772 S | 9/2002 | Lamping et al. | |
| 6,478,760 B2 | 11/2002 | Darcey | |
| 6,485,448 B2 | 11/2002 | Lamping et al. | |
| 6,659,971 B2 | 12/2003 | Gaylord | |
| D488,523 S | 4/2004 | Hamlin | |
| 6,755,800 B2 | 6/2004 | Weaver, II et al. | |
| D500,137 S | 12/2004 | Hely | |
| 6,852,088 B2 | 2/2005 | Gaylord | |
| 6,863,657 B1 | 3/2005 | Clements et al. | |
| D503,806 S | 4/2005 | Williams | |
| 6,932,781 B2 | 8/2005 | Itoi | |
| 7,189,213 B1 | 3/2007 | Weber | |
| 7,244,239 B2 | 7/2007 | Howard | |
| D580,065 S | 11/2008 | Lin | |
| D580,554 S | 11/2008 | Lin | |
| D580,556 S | 11/2008 | Lin | |
| 7,563,236 B2 | 7/2009 | Kazmierczak et al. | |
| 7,637,883 B2 | 12/2009 | Nyi | |
| 7,640,610 B2 | 1/2010 | Mervar | |
| 7,730,550 B2 | 6/2010 | Chiang | |
| 7,740,645 B2 | 6/2010 | Babaev | |
| 7,749,179 B2 | 7/2010 | Hargrave et al. | |
| D623,757 S | 9/2010 | Chiang | |
| D623,759 S | 9/2010 | Chiang | |
| D630,333 S | 1/2011 | Chiang | |
| 7,951,104 B2 | 5/2011 | Rodgers, Jr. et al. | |
| D642,280 S | 7/2011 | Goumas | |
| 8,016,780 B1 | 9/2011 | Sickles | |
| 8,043,241 B2 | 10/2011 | Goumas | |
| 8,109,273 B2 | 2/2012 | Golden et al. | |
| 8,118,765 B2 | 2/2012 | Magnuson | |
| 8,273,040 B1 | 9/2012 | Morrow | |
| 8,523,793 B1 | 9/2013 | Waldon, Sr. | |
| 8,628,488 B2 | 1/2014 | Serola | |
| 8,821,425 B2 | 9/2014 | Cox | |
| D728,805 S | 5/2015 | Tanaka | |
| D728,806 S | 5/2015 | Cox | |
| D746,997 S | 1/2016 | Higgins | |
| D750,261 S | 2/2016 | Kusmirek | |
| 9,320,639 B2 | 4/2016 | Serola | |
| 2002/0147421 A1 | 10/2002 | Darcey | |
| 2002/0169407 A1 | 11/2002 | Glinsboeckel | |
| 2003/0187373 A1 | 10/2003 | Gaylord | |
| 2005/0055775 A1 | 3/2005 | Gourd | |
| 2005/0132465 A1 * | 6/2005 | Kathumbi-Jackson | |
| | | | A41D 13/1209 |
| | | | 2/114 |
| 2005/0240134 A1 * | 10/2005 | Brown | A61F 5/0106 |
| | | | 602/26 |
| 2005/0273026 A1 | 12/2005 | Howard | |
| 2008/0188788 A1 | 8/2008 | Serola | |
| 2009/0287124 A1 * | 11/2009 | Shmidman | A61F 5/0104 |
| | | | 602/23 |
| 2010/0042031 A1 | 2/2010 | Anglada | |
| 2010/0152635 A1 | 6/2010 | Borden | |
| 2011/0009795 A1 | 1/2011 | Graham | |
| 2011/0021958 A1 | 1/2011 | Lynds | |
| 2011/0179542 A1 | 7/2011 | Khuong et al. | |
| 2011/0192403 A1 | 8/2011 | Goumas | |
| 2012/0010546 A1 | 1/2012 | Sotereanos et al. | |
| 2012/0096616 A1 | 4/2012 | Fisher | |
| 2012/0209159 A1 | 8/2012 | Fout | |
| 2012/0277649 A1 | 11/2012 | Matsuo | |
| 2013/0160176 A1 | 6/2013 | Magri | |
| 2014/0188024 A1 | 7/2014 | Cox | |

FOREIGN PATENT DOCUMENTS

| | | |
|---|---|---|
| EP | 0362528 | 4/1990 |
| EP | 0904752 | 3/1999 |
| JP | 2005245611 | 9/2005 |
| JP | 2010508072 | 3/2010 |
| KR | 100883324 | 2/2009 |
| KR | 10-20090092772 | 9/2009 |

(56) References Cited

FOREIGN PATENT DOCUMENTS

| | | |
|---|---|---|
| WO | 2008051640 A2 | 5/2008 |
| WO | 2008051640 A3 | 5/2008 |

OTHER PUBLICATIONS

European Search Report for Application No. EU13867118.5 (dated Aug. 5, 2016).
Written Opinion and International Search Report for PCT/US2013/078429 (dated Apr. 3, 2014).

* cited by examiner

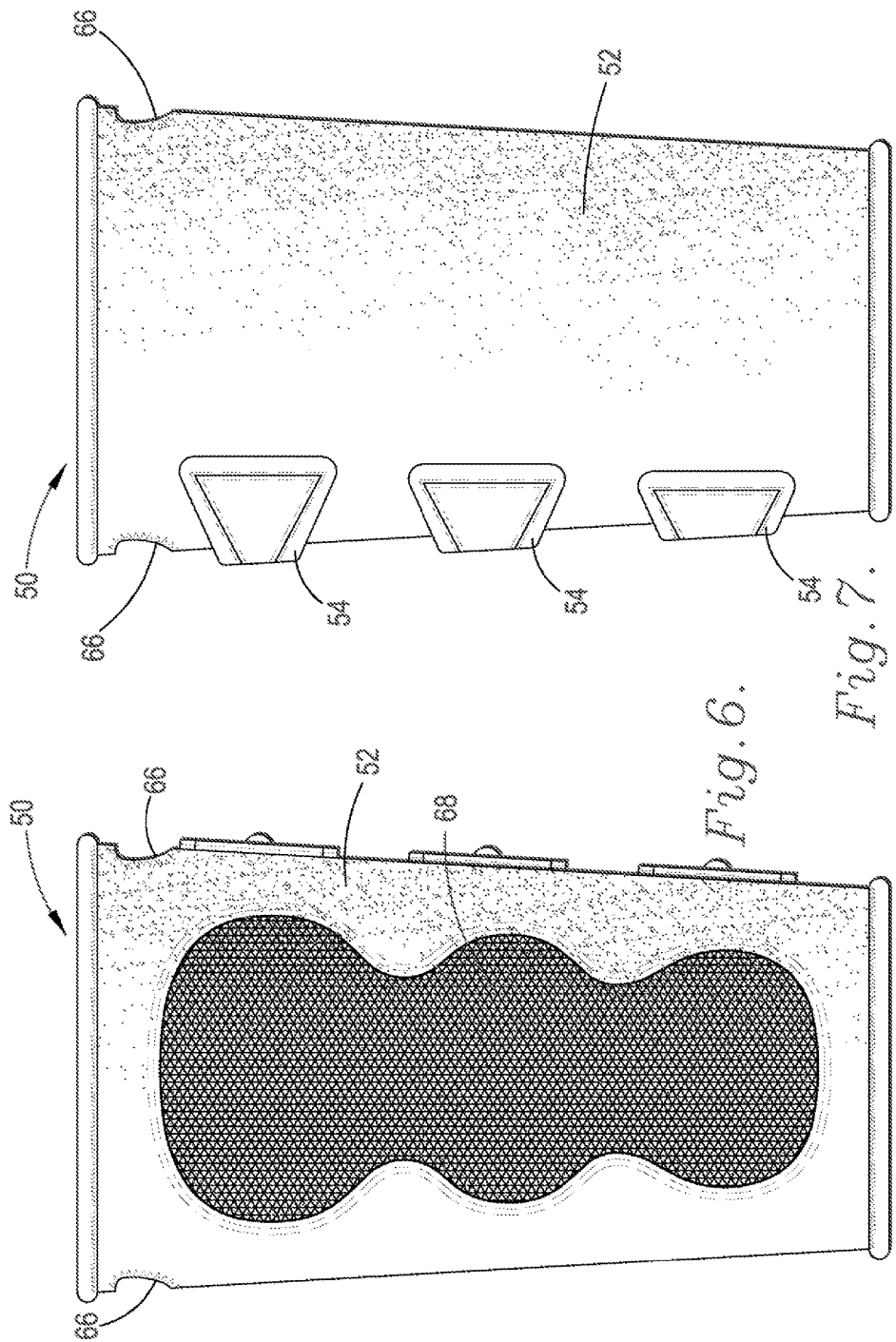

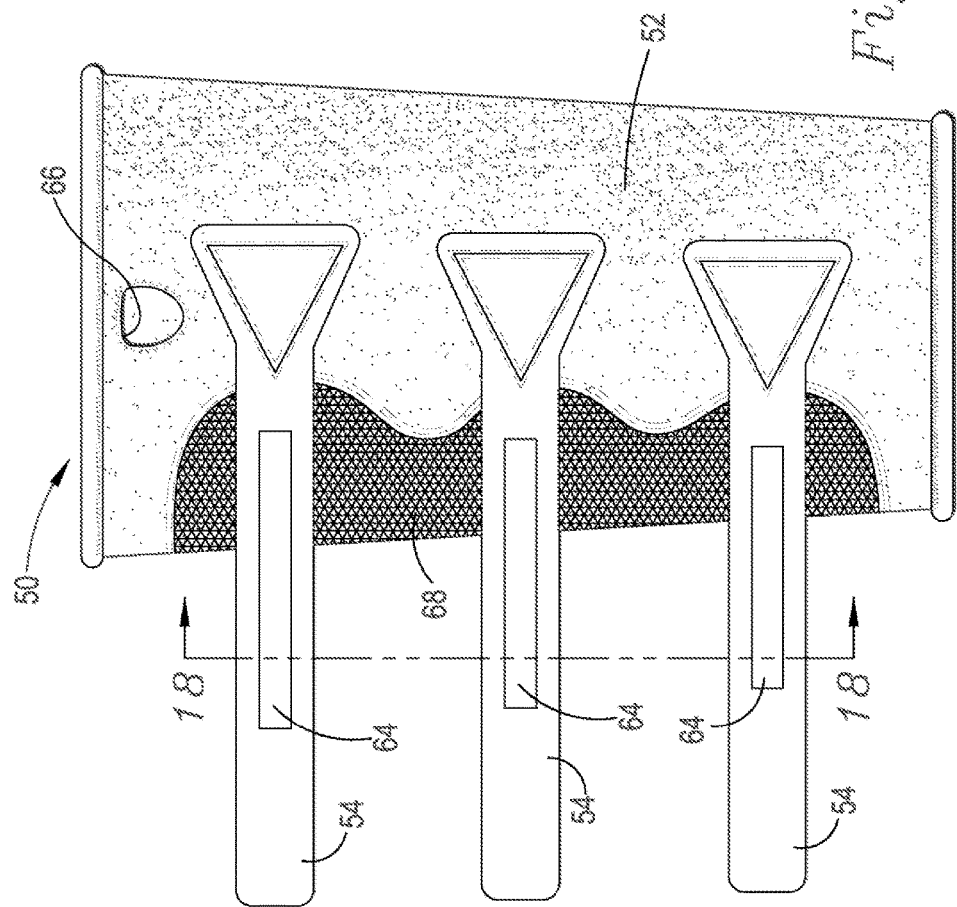

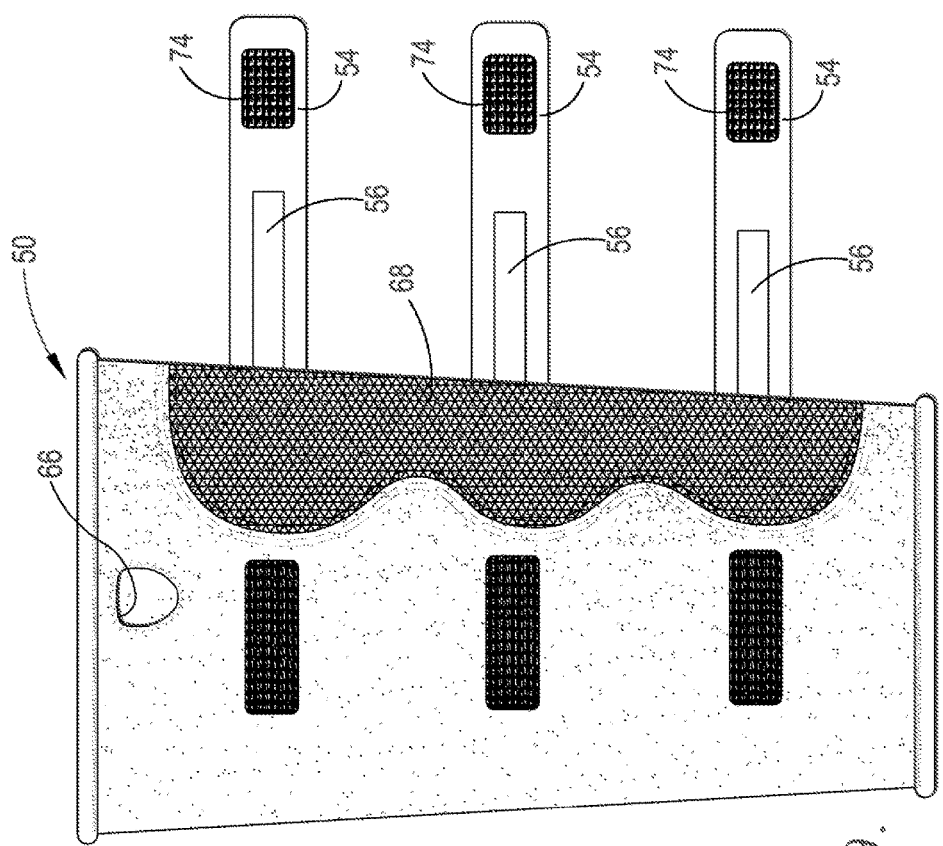

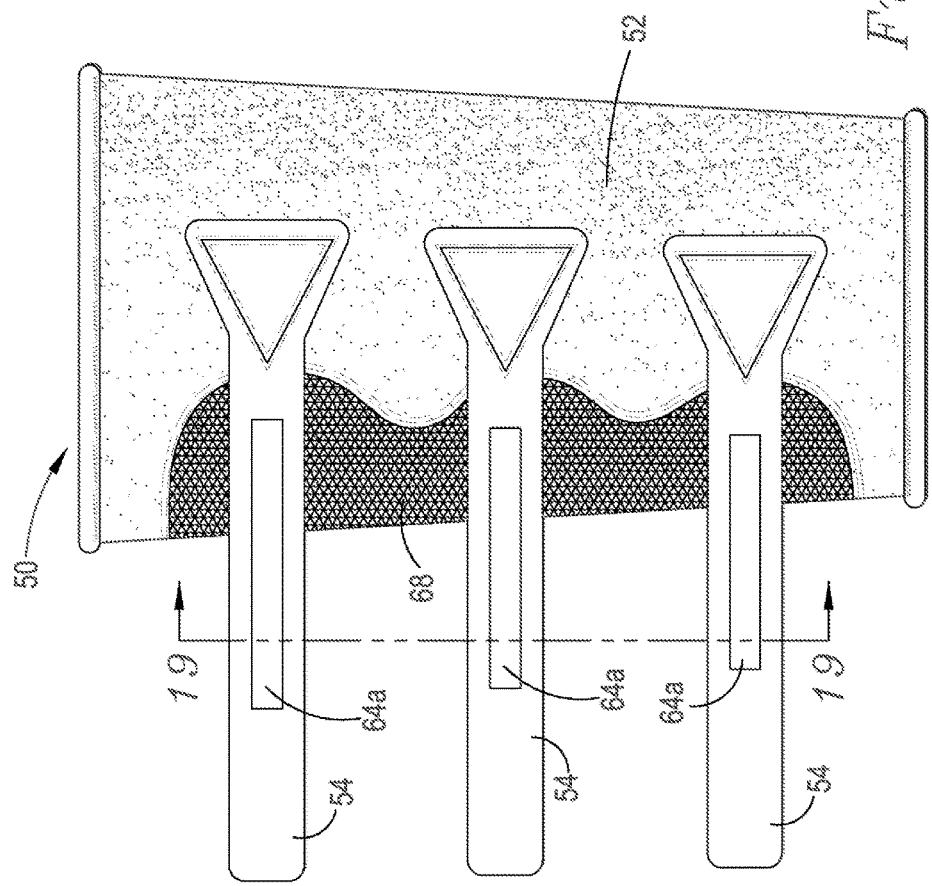

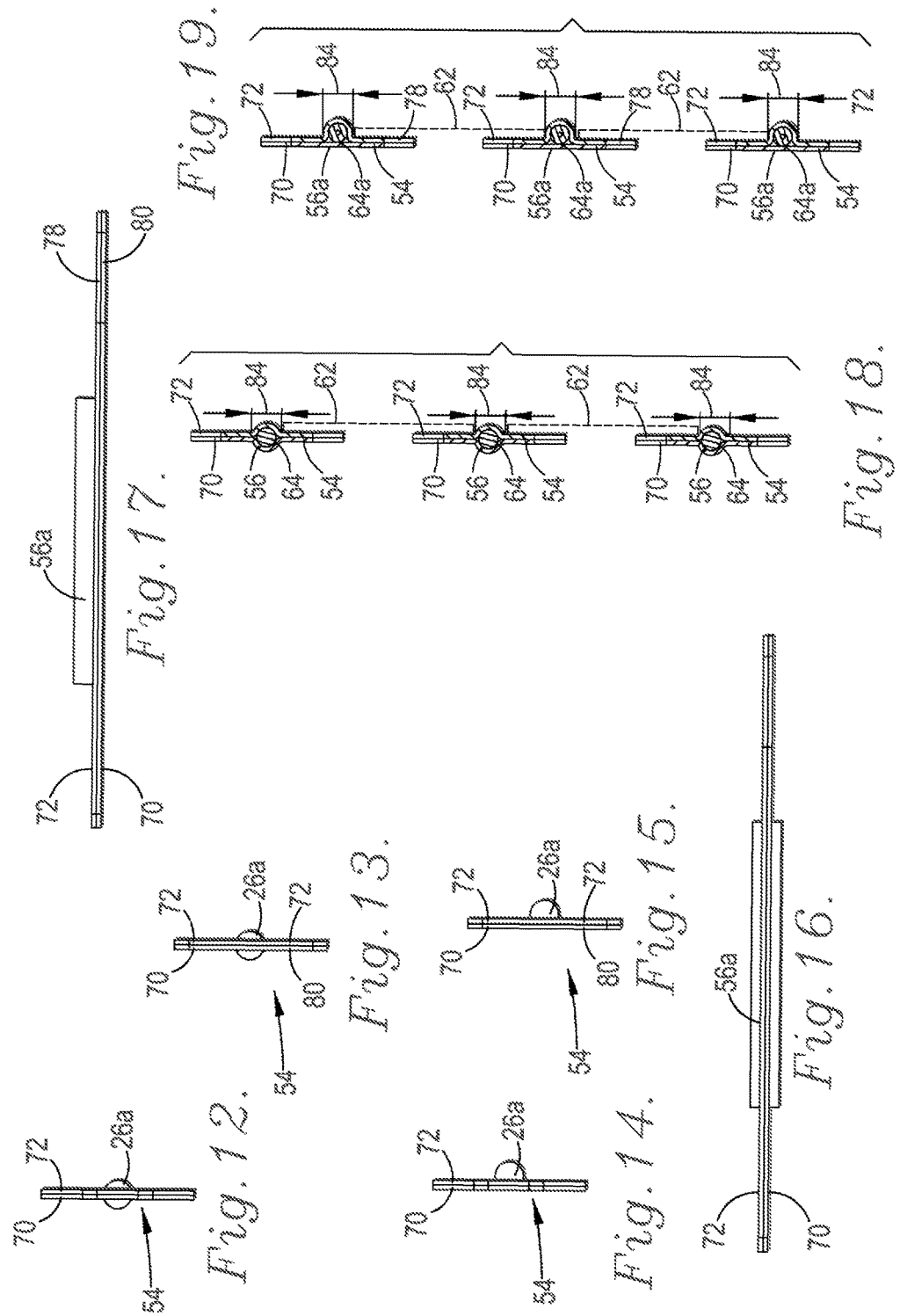

DEVICE AND METHOD FOR APPLYING PRESSURE TO A MAMMALIAN LIMB

CROSS REFERENCE TO RELATED APPLICATION

This is a continuation-in-part of U.S. patent application Ser. No. 14/022,998, entitled A DEVICE AND METHOD FOR APPLYING PRESSURE TO A MAMMALIAN LIMB, filed on Sep. 10, 2013, the entire disclosure of which is incorporated by reference herein.

BACKGROUND OF THE INVENTION

The present invention relates generally to therapeutic devices. More specifically, the invention relates to a therapeutic pressure band for applying pressure to a mammalian limb. Particularly, the invention relates to a therapeutic pressure band for applying pressure across muscles near the insertion point of those muscles (i.e., near where the muscle inserts into the bone) and/or across the bone itself. Such devices are commonly used to provide pain relief for inflamed and painful muscles, tendons and joint capsules and are especially used for treating medial tibial stress syndrome, also known as "shin splints."

The pathological condition generally known as shin splints afflicts many people. In many instances, shin splints (and other forms of tendonitis) is caused by overexertion and overloading of a muscle group during exercise, sports or simple repetitive motion. For example, if a person begins running extended distances after not running for a period of time, the tendons and muscles of the person's legs, especially the gastrocnemius, soleus, and plantar muscles, may be unable to absorb the impact of the shock force as they become fatigued. In particular, repetitive stress of the impact forces may eccentrically fatigue the soleus and create repeated tibial bending or bowing. In some instances, pressure across the tibia, and in some cases the fibula, will increase to a point where the bone will be painful as well.

Orthopedists observe that many patients having various forms of tendonitis and/or muscle inflammation, and particularly those having shin splints, experience pain relief when pressure is applied across the inflamed muscles, tendons, and bones. For those patients with shin splints placing a compressive band around the lower leg between the knee and ankle may provide some relief. Such bands are also utilized during use of the leg (e.g., jogging or repetitive movement at work) to dampen muscle movement and thereby reduce additional inflammation of the muscles and tendons.

However, the mammalian body is a very dynamic system. Treatments, braces, and straps that provide relief for one patient often do not provide relief for another, which is one reason there is such a large number of orthopedic devices on the market for all types of orthopedic conditions. Accordingly, there is a continuing need for new and innovative orthopedic devices to provide treatment and relief to those patients that do not respond to known treatment methods.

SUMMARY OF THE INVENTION

In one aspect, the invention is a therapeutic pressure band for applying pressure to a limb. The pressure band comprises a plurality of flexible straps for encircling a limb and a connecting material extending between each adjacent strap to secure the straps together. The straps each have adjustable cooperative fasteners proximate their ends for adjustably fastening the straps about the limb. A plurality of elongated pressure members are attached to the band and positioned between the adjustable cooperative fasteners. Each flexible strap includes one elongated pressure member attached thereto, and the pressure members are separated from each other by a distance and oriented substantially perpendicular to a longitudinal axis of the limb. During use, each pressure member creates a discrete line of pressure across the limb.

In another aspect, the invention is a method of simultaneously applying a plurality of discrete lines of pressure to a limb. The method comprises the steps of encircling the limb with a pressure band, with the band having a plurality of flexible straps and with each of the straps having adjustable cooperative fasteners proximate ends of the straps for adjustably fastening the straps about the limb. The band also has a plurality of elongated pressure members, with each of the straps having one pressure member attached thereto. The pressure members are separated from each other by a distance and oriented substantially perpendicular to a longitudinal axis of the limb when the band is in use. The method also includes the step of adjusting the cooperative fasteners of each of the straps to tighten the band around the limb thereby compressing each pressure member against the limb to create discrete lines of pressure across the limb.

A still further aspect of the invention is a method of applying a plurality of independent lines of pressure to a limb. The method comprises the steps of placing a plurality of elongated pressure members against the limb, with each of the pressure members including a force transfer surface, and wherein each of the elongated pressure members are operable to apply a line of pressure that is independent of lines of pressure being applied by other pressure members. The steps additionally include creating a plurality of circumferential compressive forces around the limb. The steps further include concentrating a portion of each of the plurality of the compressive forces at the force transfer surface of each of the pressure members.

BRIEF DESCRIPTION OF THE DRAWINGS

These and other more detailed and specific features of the present invention are more fully disclosed in the following specification, reference being had to the accompanying drawings, in which:

FIG. 6 is a front elevational view of the pressure device from FIG. 5.

FIG. 7 is a rear elevational view of the pressure device from FIGS. 5-6.

FIG. 8 is a left side elevational view of the pressure device from FIGS. 5-7.

FIG. 9 is a right side elevational view of the pressure device from FIGS. 5-8.

FIG. 10 is a left side elevational view of an additional embodiment of a therapeutic pressure device according to embodiments of the present invention.

FIG. 12 is a front elevational view of a strap of the pressure device from FIGS. 5-9.

FIG. 13 is a rear elevational view of the strap from FIG. 12.

FIG. 14 is a front elevational view of a strap of the pressure device from FIGS. 10-11.

FIG. 15 is a rear elevational view of the strap from FIG. 14.

FIG. 16 is a top elevational view of the strap from FIGS. 12-13.

FIG. 17 is a top elevational view of the strap from FIGS. 14-15.

FIG. 18 is a cross-sectional view of straps of the pressure device shown in FIG. 8 taken along the line 18-18.

FIG. 19 is a cross-sectional view of straps of the pressure device shown in FIG. 10 taken along the line 19-19.

DETAILED DESCRIPTION OF THE INVENTION

In the following description, for purposes of explanation, numerous details are set forth, such as device configurations and movements, to provide an understanding of one or more embodiments of the present invention. Furthermore, the following detailed description is of the best presently contemplated mode of carrying out the invention. The description is not intended in a limiting sense, and is made solely for the purpose of illustrating the general principles of the invention. The various features and advantages of the present invention may be more readily understood with reference to the following detailed description taken in conjunction with the accompanying drawings.

While the invention is described with respect to various embodiments thereof, it will be understood by those skilled in the art that various changes in detail may be made therein without departing from the spirit, scope, and teaching of the invention. Accordingly, the invention herein disclosed is limited only as specified in the claims.

Figure 1A:
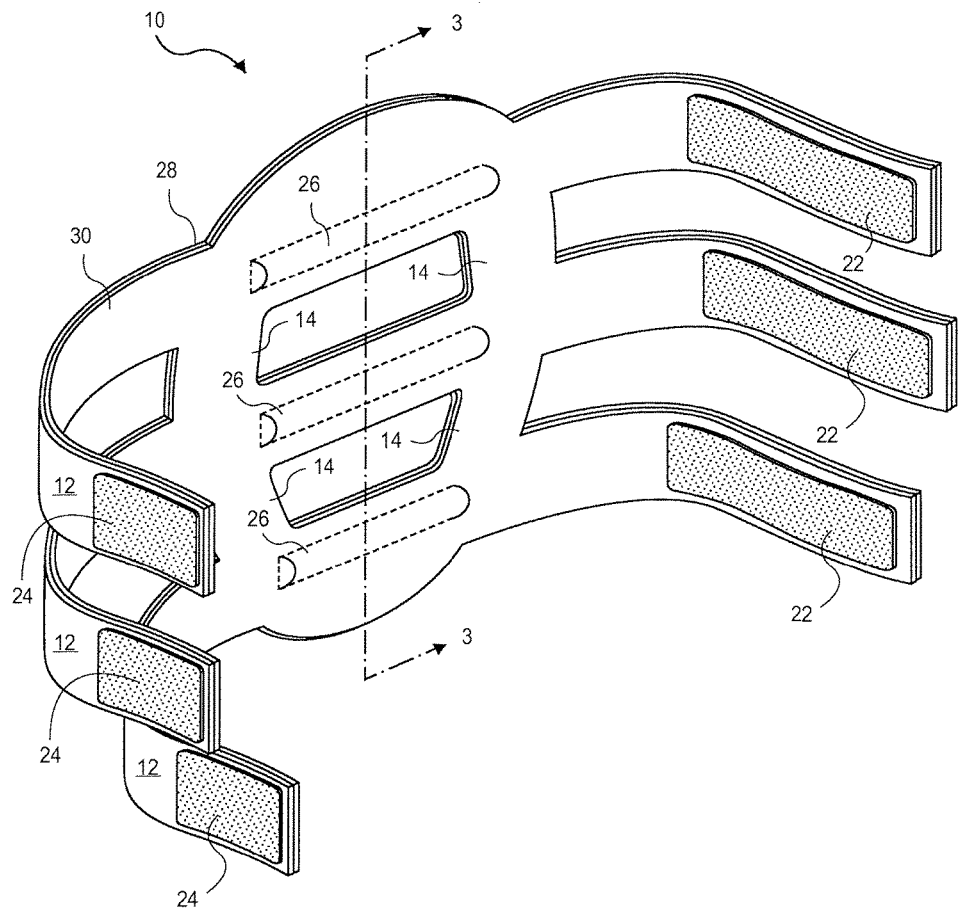
FIG. 1A is a perspective view of an embodiment of the invention.
Figure 1B:
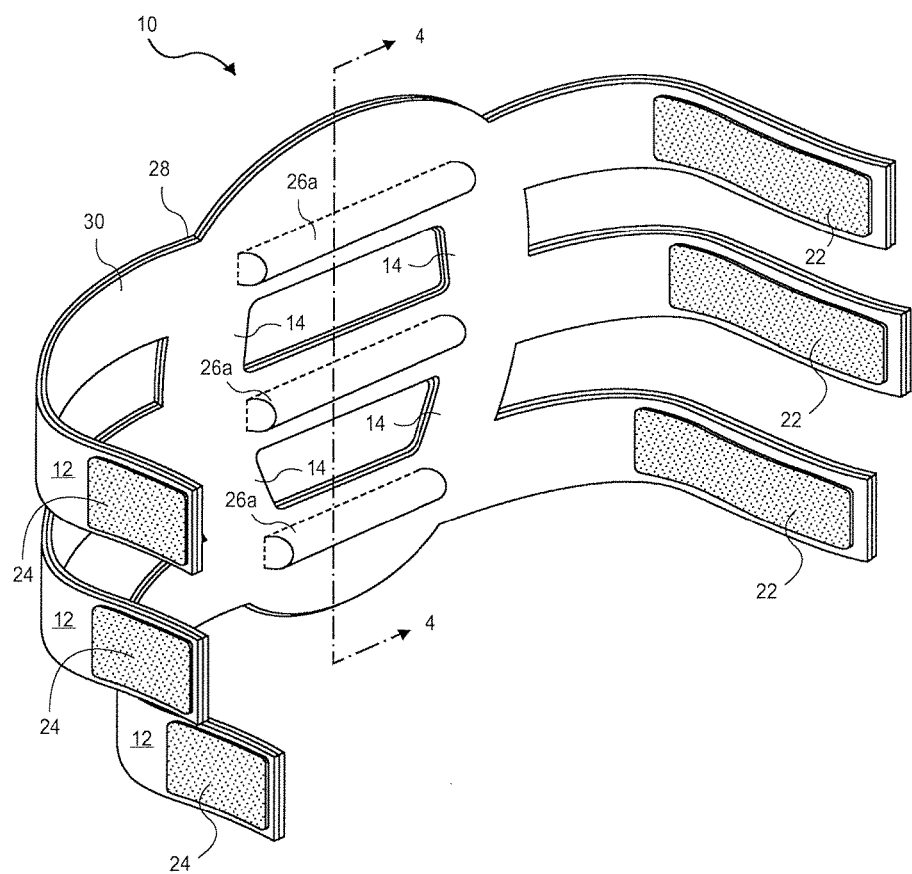
FIG. 1B is a perspective view of an alternative embodiment of the invention.

Referring now to the drawings in detail, where like numerals refer to like parts or elements, there is shown in FIGS. 1A and 1B a therapeutic pressure band generally designated by the numeral 10. The pressure band 10 is designed to apply pressure to the muscles and/or bones of a limb (not shown). For ease of discussion the detailed description describes an embodiment of the invention in the context of a band used in the treatment of shin splints in a human. This narrative convenience should not be interpreted as limiting the scope of the invention. The band 10 of the present invention includes means for applying a plurality of discrete lines of pressure to the muscles, tendons, and/or bones of a limb. Those skilled in the art recognize that depending upon the placement of the band, the lines of pressure provided by the band will be above muscle, tendon, bone, the transition area between the muscle and the tendon, and/or the transition areas between the muscle, tendon, and bone. Therefore, as used herein and for clarity, the term muscle or muscles includes the primarily fibrous portions of a muscle, commonly known as tendons, which attach the muscle to bone as well as the contractive tissue commonly referred to as muscle.

In more detail, the pressure band 10 according to embodiment of the present invention broadly comprises a plurality of elongated flexible straps 12 of sufficient length such that the pressure band is capable of encircling the limb to be treated. The pressure band 10 includes connection material 14 that extends between and connects the straps 12 together. In certain embodiments, the pressure band 10 also includes a plurality of adjustable cooperative fasteners proximate ends of the each of the plurality of straps 12 for adjustably fastening and/or securing the straps and thus the pressure band about the limb, for creating a compressive force or pressure about the limb, and for adjusting the force/pressure applied to the limb. Each of the pressure straps 12 contains a pocket 26, 26a that is integral with the strap. In certain embodiments, the pockets 26, 26A located on adjacent straps 12 are separated from each other by a distance 32. In certain embodiments, an elongated pressure member 34, 34a contained within each of the pockets 26, 26A. During use of the pressure band 10 in certain embodiments, the pressure members 34, 34a are oriented substantially perpendicular to a longitudinal axis of the limb and each pressure member creates a distinct line of pressure across the muscles and/or bone of the limb. Each element is discussed in more detail below.

Of note, some embodiments of the present invention include features similarly found in certain portions of the inventive concepts disclosed in co-pending application U.S. Ser. No. 13/731,289 filed on Dec. 31, 2012, and entitled "A DEVICE AND METHOD FOR APPLYING PRESSURE TO A MAMMALIAN LIMB," the entire disclosure of which is herein incorporated by reference into the present application.

In certain embodiments, the pressure band 10, including portions the flexible straps 12 and the connecting material 14, are constructed of a suitable flexible material such as woven fabric, vinyl, leather, neoprene, nylon, etc. In some embodiments, the material utilized to construct the band 10 has some elastic qualities, or in other embodiments, the material is mostly inelastic. If elastic materials are utilized, then care should be taken when the band 10 is applied to a limb because elastic materials make it easier to inadvertently cut off blood circulation to a limb. In certain embodiments, the pressure band 10 is mostly made of a single material for ease of manufacture or, in alternative embodiments; it is made from a combination of materials where the materials are chosen for specific purposes. For example in some embodiments, one portion of the band 10 is formed from relatively inelastic leather while another portion is formed from somewhat elastic neoprene. In certain embodiments, a portion or multiple portions of the band 10 are formed of solid materials (e.g., thin polymer sheets) to add strength to the strap or focus pressure in a particular area.

The architecture of the plurality of straps 12 can vary considerably. In certain embodiments, the straps 12 are formed of a single layer of material, or in alternative embodiments, the straps 12 are made of multiple layers of material. If a single layer of material is used, slight adjustments in the manner of attaching the pressure members 34, 34a (discussed below) to the straps 12 are necessary. Such adjustments are well within the knowledge of those skilled in the art.

In preferred embodiments the straps 12 are formed of multiple layers as shown in FIGS. 1A and 1B. The band 12 shown in the figures comprises a first layer 28 attached to a second layer 30. In other embodiments, additional layers can be utilized if desired. For example, in some embodiments, a layer of foam is added to provide comfort for the user.

The therapeutic pressure band 10 includes adjustable cooperative fasteners proximate the ends of each of the straps 12 for adjustably fastening the band about the limb to create compressive forces or pressures about the limb and for adjusting the forces/pressures applied to the limb. In certain embodiments, such as illustrated in the drawings, a Velcro type fastener is utilized on the ends of the straps 12, including a strip of hook portion 22 on a first end and a strip of fiber loop portion 24 on a second end. In other embodiments, a single, large piece of Velcro (either a hook portion or a loop portion) extends between and connects together each of the straps 12 on their first end. As such, the second ends of each of the straps 12, which also include Velcro, are capable being fastened to the large piece of Velcro. Although Velcro type fasteners are preferred due to ease of use, in other embodiments, other types of fasteners such as buckles, snaps, latches, or the like can be used in the practice of the invention. For example, in certain embodiments, a metal or polymeric loop is attached to a first end of a strap 12 via a small tube extending across the first end of the strap, and a second end of the strap is capable of being inserted through loop and secured in place with Velcro, prongs, clasps, or the like.

As illustrated by FIGS. 1A and 1B, the straps 12 of the band 10 are secured together and interconnected by the connecting material 14. In certain embedment's, such as those shown in the drawings, the connecting material 14 extends between the straps 12, such that the connecting material 14 presents an egg-shaped or oval-shaped form. The egg-shaped or oval-shaped form may be preferred in embodiments in which the band 10 is secured to a user's lower log leg, such as for instance to treat shin splints. As such, the egg-shaped form or oval-shaped form corresponds to a shape of the user's lower leg to facilitate proper placement and fit. In other embodiments, the connecting material 14 extends between the straps 12, such that the connecting material presents other-shaped forms, such as circular, triangular, rectangular, or the like.

Figure 2:
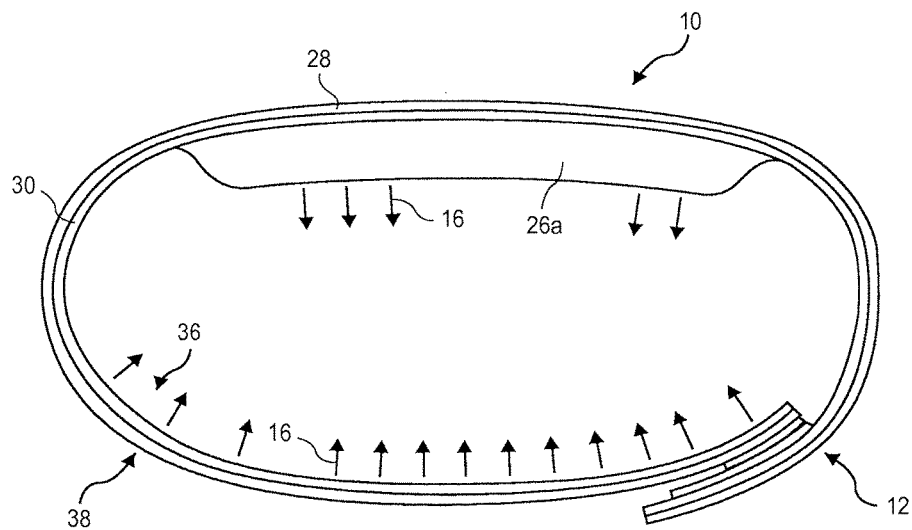
FIG. 2 is a top plan view of the embodiment of FIG. 1B.

FIG. 2 illustrates the engagement of the fasteners of the band 10 and how such an engagement creates compressive forces/pressures around a limb. As the ends of the straps 12 are secured together, the circumference of the band 10 contracts causing compressive forces around the interior of the band. These forces are illustrated by the force vector arrows 16 shown in FIGS. 2, 3 and 4 and are discussed in more detail below.

In one embodiment of the band 10 according to the invention the means for applying a plurality of discrete lines of pressure to a limb comprise the plurality of pockets 26, 26a that are integral to each of the straps 12. In certain embodiments, the pockets 26, 26a are formed within the straps 12, or in alternative embodiments, are formed separately and attached to the straps 12.

In certain embodiments, the manner in which the pockets 26, 26a are formed vary with the methods used to manufacture the band 10. For example, in the embodiment of the invention shown in FIGS. 1A and 3, the band 10 is formed of multiple layers of material. In this embodiment the band 10, and more specifically the straps 12, is formed of a first layer 28 of material attached to a second layer 30 of material. The method of attaching the first layer 28 to the second layer 30 includes any method known in the art such as sewing or gluing. Those skilled in the art can pick the method of attachment that is most suitable for the materials used to construct the band 10.

Figure 3:
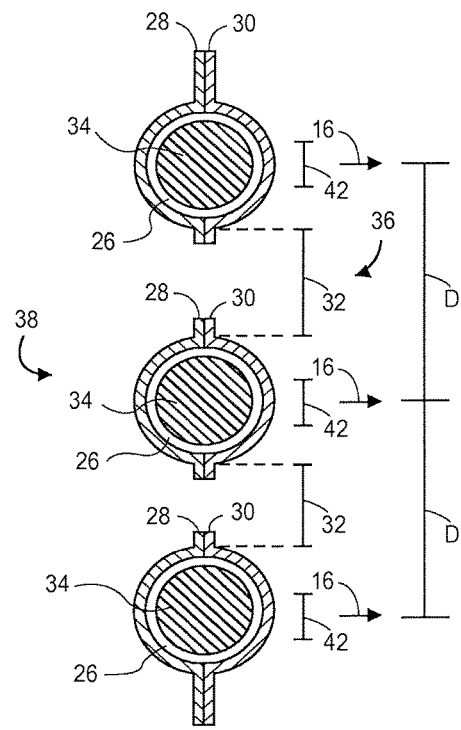
FIG. 3 is a view taken on lines 3-3 of FIG. 1A.

In the embodiment shown in FIG. 3 the first 28 and second 30 layers are joined by sewing the layers together. The pockets 26 are located intermediate the first and second layer 28, 30 in the potential space that exists between the layers. In the embodiment shown in FIG. 3 there exist three pockets 26 formed between the layers 28, 30 and extending longitudinally along each of the straps 12. In certain embodiments, the pockets 26 are completely enclosed, or in other embodiments, they have small openings (not shown) at one end. Providing small openings allows the user to change out the pressure members (described in more detail below) that reside therein (e.g., remove a more rigid member for a more compliant member).

Figure 4:
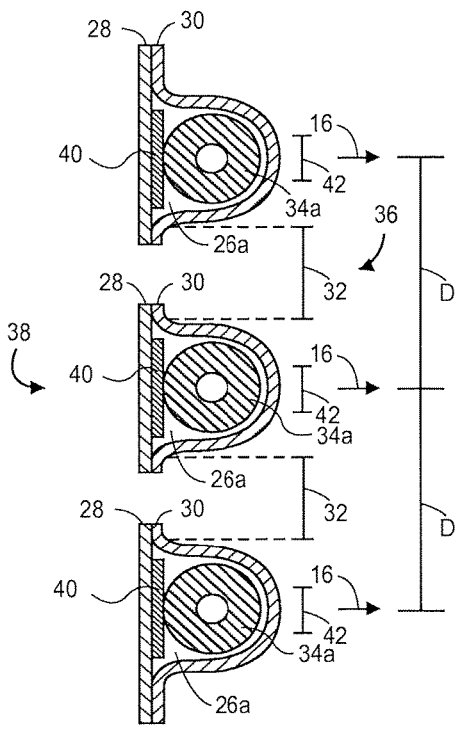
FIG. 4 is a view taken on lines 4-4 of FIG. 1B.

Turning now to FIG. 4, in an alternative embodiment, the band 10, and more specifically the straps 12, is constructed such that the pockets 26a are primarily arranged to be on one side of the straps 12. In both embodiments and particularly the embodiment shown in FIGS. 3 and 4, the band 10 can be described as having an inside surface 36 and an outside surface 38 where the inside surface 36 faces the limb as shown in FIG. 2. In the embodiments shown in FIG. 4, the pockets 26a are positioned primarily on the inside surface 36 of the band 10. In some embodiments, the pockets 26a have small openings (not shown) that allow a user to change out pressure members.

The pockets 26a shown in FIG. 4 are similar to the pockets shown in FIG. 3 in that they are positioned intermediate a first 28 and second 30 layer. They are different in that the portion of the straps 12 that is between pressure members 34a and the outside surface 38 is reinforced to be more rigid and less capable of deforming to conform to the shape of the pressure member 34a as shown in FIG. 4.

In embodiments of the present invention, the reinforcement of the straps 12 to form the style of pockets 26a shown in FIG. 4 takes several forms. One option is to place a backing plate 40 intermediate the pressure members 34a and the outside surface 38. In certain embodiments, the backing plate 40 is semi-flexible (for example, a thin piece of plastic). In other embodiments, the backing plate 40 is formed from a rigid material that has a curvature to conform to the natural curvature of the limb. Another alternative embodiment for reinforcing the straps 12 is to use multiple layers of material (e.g., fabric, leather) to create the "outer" portion the straps. Either method of reinforcement, results in pockets 26a that generally protrude toward the inside of the band 10.

The pressure members 34, 34a used in the practice of the invention are sized to fit within the pockets 26, 26a. The pressure members are elongated to provide continuous lines of pressure that extend for a distance across a muscle, muscle group, and/or bone of a limb. Those skilled in the art recognize that the pressure (and force vectors) applied by the pressure members 34, 34a to a limb extends along lines that are generally perpendicular to the longitudinal axis of the limb.

Pressure members having a circular or hemispherical cross-section are preferred because they create a generally smooth and uniform force transfer surface (generally represented by numeral 42) when compressed against a limb. In other embodiments, other cross sections (for example, hexagonal or star shaped) are used in the practice of the invention and may provide more relief for some patients. In addition, embodiments provide for the pressure members 34, 34a to be either solid or hollow as shown in FIGS. 3 and 4 respectively. Similarly, embodiments provide for the material used to construct the pressure members to vary depending upon the amount of pressure desired. For example, a hollow tube of very flexible and soft rubber would have a pressure distribution profile that is different from a solid tube of fairly rigid nylon. One patient may prefer one type of pressure member over another.

In certain embodiments, each of the pressure members 34, 34a on the straps 12 will have similar lengths. For instance, in some specific embodiments, each of the pressure members 34, 34a will have a length within a range from about 2 inches to about 4 inches. In certain specific embodiments, each of the pressure members 34, 34a will have lengths that are about 2.25 inches, 2.75 inches, or 3.00 inches. In certain other embodiments, one or more of the pressure members 34, 34 of the straps 12 will have different lengths. For instance, in certain embodiments in which the band 10 is positioned on a user's lower leg, the pressure members 34, 34a that are positioned higher will be longer than the pressure members 34, 34a that are positioned lower. With reference to FIGS. 1A and 1B, for example, the pressure members 34, 34a positioned near an upper portion of the band 10 are longer than the pressure members 34, 34a positioned near a lower portion of the band. Such embodiments may be beneficial for use on a user's leg because a width of the user's leg generally decreases moving from an upper portion of leg to a lower portion leg. In certain embodiments in which the pressure members 34, 34a are of different lengths, a first pressure member that is positioned directly below a second pressure member will have a length that is about 95 percent, 90 percent, 85 percent, 80 percent, 75 percent, or less than the length of the second pressure member. In certain specific embodiments of the band 10, such as illustrated in the drawings and that include three straps 12 and 3 pressure members 34, 34a, the band will include an upper pressure member that is about 3.00 inches long, a middle pressure member that is about 2.75 inches long, and a bottom pressure member that is about 2.25 inches long.

In all embodiments of the band 10, the pockets 26, 26a are separated from each other by a distance 32. The length of the distance 32 is that which is sufficient to create a plurality of separate and discrete lines of pressure across the band 10. Stated alternatively, the pressure members do not touch or adjoin or abut to create a single, concentrated, uniform area of pressure when the band is applied to a limb. Stated in yet a further alternative, the lines of force vectors 16 created by the pressure members 34, 34a and which are directed toward the limb are separated by a distance "D" that is greater than the sum of the radii of any two adjacent pressure members 34, 34a. Stated more simply, there is a gap between adjacent pressure members 34, 34a.

Embodiments of the present invention provide for the distance between the pockets and pressure members to vary depending upon the size of the pressure members, the width of the straps, the pocket material thickness, and the size of the limb. For those bands used in the treatment of shin splints, embodiments provide for the distance 32 to range between about ¾ inch to about 2 inches or greater. In other embodiments, the distance 32 ranges between about ¼ inch to about ¾ inch. In still other embodiments, the distance 32 ranges from about 2 inches to about 4 inches. Furthermore, it is envisioned that a certain distance 32 that provides relief for some patients will not provide relief for other patients. Thus, it is expected that bands 10 that include various sizes and distances 32 will be manufactured in accordance with the practice of the invention.

As described, embodiments of the present invention allow for the pressure members 34, 34a to apply discrete lines of pressure to muscle, tendon, and/or bone of a limb. In particular, the lengths of the pressure members 34, 34a (as described above) and the separation distance between the pressure members (as described above), allow for the discrete lines of pressure to be applied to the limb in a plurality of arrangements. For example, in some embodiments, all of the band's 10 pressure members 34, 34a will be applied only to the muscles or muscle group of the limb, only to the tendon of the limb, or only to the bone of the limb. In other embodiments, one or more of the pressure members 34, 34a will be applied to the muscles or muscle group of the limb, while one or more other of the pressure members will simultaneously be applied to the tendons that connect the muscle or muscle group to the bone of the limb. In still further embodiments, one or more of the pressure members 34, 34a will be applied to the muscles, muscle group, and/or tendon of the limb, while one or more other of the pressure members will simultaneously be applied to the bone of the limb. Such varying arrangements for the application of the pressure members 34, 34a are due, in part, to the placement, length, and separation of each of the pressure members of the band 10 according to embodiments of the present invention.

Another aspect of the invention is a method of simultaneously applying a plurality of discrete lines of pressure to the muscles and/or bone of a limb such as a human leg. The method comprises the step of encircling a limb with an elongated band such as the band 10 with the plurality of straps 12 discussed above. In particular, the band utilized in the method has adjustable cooperative fasteners proximate the ends of the straps for adjustably fastening the band about the limb. The band also possesses a plurality of elongated pressure members, such as those described previously, where the pressure members are separated by a distance and oriented substantially perpendicular to the longitudinal axis of the limb when the band is in use. The pressure members are preferably retained within discrete pockets that are integral to the straps of the band as discussed previously.

The method continues by adjusting the cooperative fasteners for each of the straps to tighten the band around the limb thereby compressing each pressure member against the limb to create discrete lines of pressure across the muscles and/or bone of the limb where the lines of pressure are separated by a distance. Because each of the straps includes its own pressure member, embodiments of the present invention provide for a user to independently adjust a magnitude of the pressure applied via each the pressure members. As such, the band of the present invention is capable of applying varying magnitudes of pressure for each of its straps and pressure members, such that a user can customize the applied lines of pressure as may be required for the user's individual needs. For example, if a user applies the band 10 of embodiments of the present invention to the user's shin to treat shin splints, the user can individually adjust the amount of pressure applied to the user's leg via each pressure member 34, 34a. In more detail, if an upper portion of the user's shin is more inflamed than a lower portion, the user can apply greater pressure to the upper portion than the lower portion. Specifically, the user can adjust the cooperative fasteners of the straps 12 so that upper straps are fastened tighter than lower straps. As such, the pressure members 34, 34a associated with the upper straps will impart greater pressures, than the pressure members associated with the lower straps.

In yet another aspect, the invention is a method of simultaneously applying a plurality of discrete lines of pressure to the muscles and/or bone of a limb. The method comprises the step of placing a plurality of discrete elongated pressure members against a limb where the elongated pressure members are the same as those discussed in relation to the pressure band 10 according to the invention. When the band is in use the elongated pressure members are substantially perpendicular to the longitudinal axis of the limb and are separated from each other by a distance. The pressure members also have a force transfer surface that extends for a distance across the surface of the limb.

The method continues with the step of creating a circumferential compressive force around the limb. This step is typically accomplished by tightening the band 10 around the limb to create compressive forces similar to those illustrated in FIG. 2. Tightening the straps 12 of the band 10 forces the pressure members, more specifically the force transfer surfaces 42 of the pressure members 34, 34a into the limb, which concentrates a portion of the compressive force applied to the limb at the force transfer surface 42. This in turn creates the continuous lines of pressure that aid in dampening movement of the muscles, tendons, and/or bone.

In addition to the therapeutic pressure band 10 described above, embodiments of the present invention also include a pressure device for applying multiple types of pressure to a limb. An example of pressure devices according to embodiments of the present invention are illustratively shown in FIGS. 5-11, and generally designated by the numeral 50. The pressure device 50 is designed to apply pressure to the muscles and/or bones of a limb (not shown). As with the pressure band 10 described above, the following discussion describes an embodiment of the invention in the context of a device used in the treatment of shin splints in a human. This narrative is provided for convenience and should not be interpreted as limiting the scope of the invention. The pressure device 50 of the present invention includes means for applying both an area of compressive force around a portion of the limb and a plurality of discrete lines of pressure to the muscles, tendons, and/or bones of a limb. Those skilled in the art recognize that depending upon the placement of the pressure device 50, the area of compressive force and the lines of pressure provided by the device will be above muscle, tendon, bone, the transition area between the muscle and the tendon, and/or the transition areas between the muscle, tendon, and bone. Therefore, as used herein and for clarity, the term muscle or muscles includes the primarily fibrous portions of a muscle, commonly known as tendons, which attach the muscle to bone as well as the contractive tissue commonly referred to as muscle.

Figure 5:
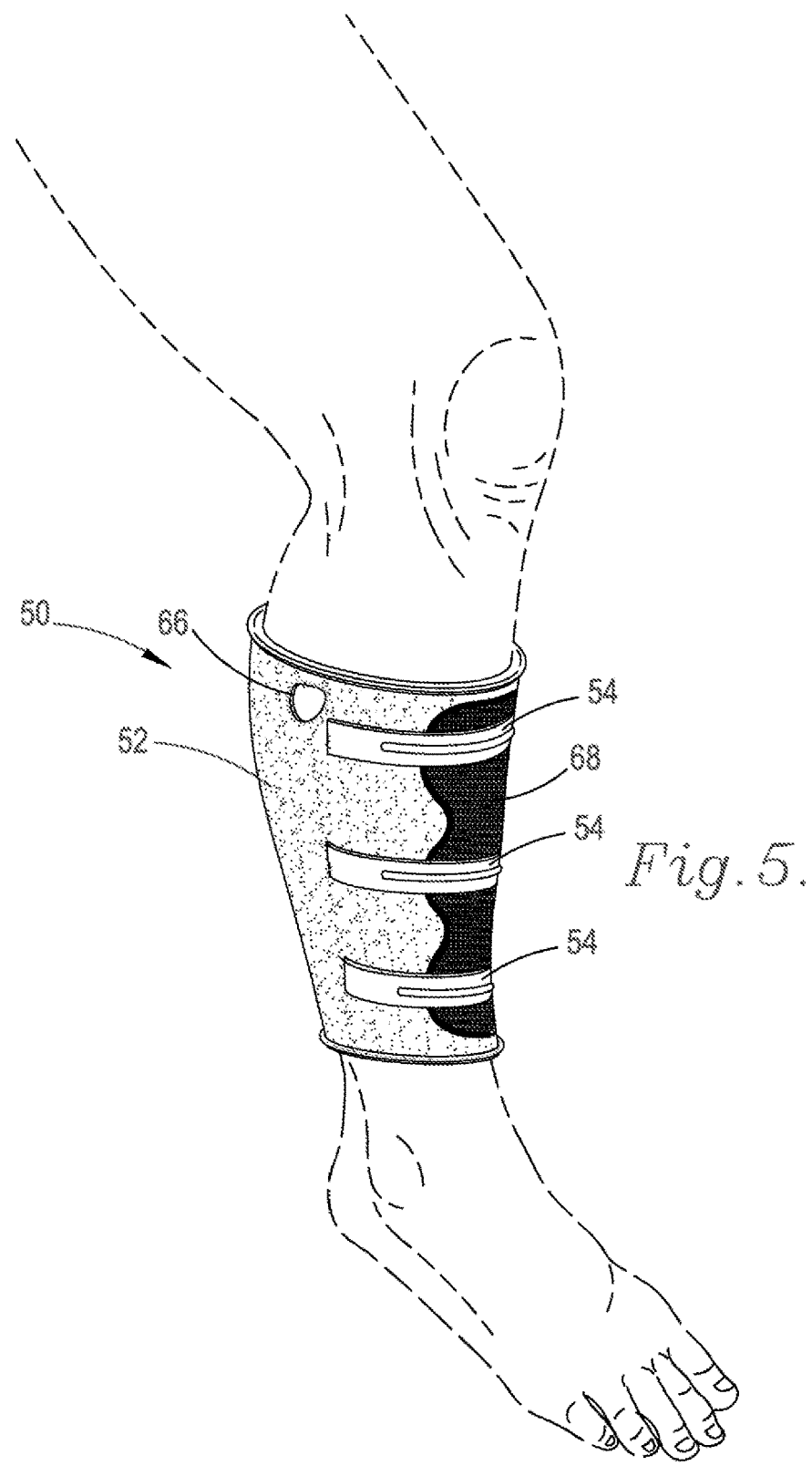
FIG. 5 is a perspective view of a therapeutic pressure device according to embodiments of the present invention, with the pressure device shown positioned on a limb of a user.

In more detail and as illustrated in FIG. 5, the pressure device 50 according to embodiment of the present invention broadly comprises a compressive sleeve 52 capable of being placed over a limb (such as an arm or a leg), so as to create an area of compressive force about the limb, and a plurality of elongated flexible straps 54 attached to the sleeve and capable of being adjustably positioned so as to create individual lines of pressure across the limb. As illustrated in FIGS. 5-11, the sleeve 52 of the pressure device 50 is generally cylindrical in shape and formed from a dry-fit, breathable material, such as woven fabric, neoprene, spandex, nylon, other polyamides, or combinations thereof. Each of the straps 54 is secured to an exterior surface of the sleeve 52 via a first end of the strap. In certain embodiments, and as will be discussed in more detail below, the pressure device 50 includes a plurality of adjustable cooperative fasteners located on the sleeve 52 and on a second end of each of said straps 54 for adjustably fastening and/or securing the straps and about the sleeve and the user's limb, for creating a compressive force or pressure about the limb, and for adjusting the force/pressure applied to the limb.

Figure 11:
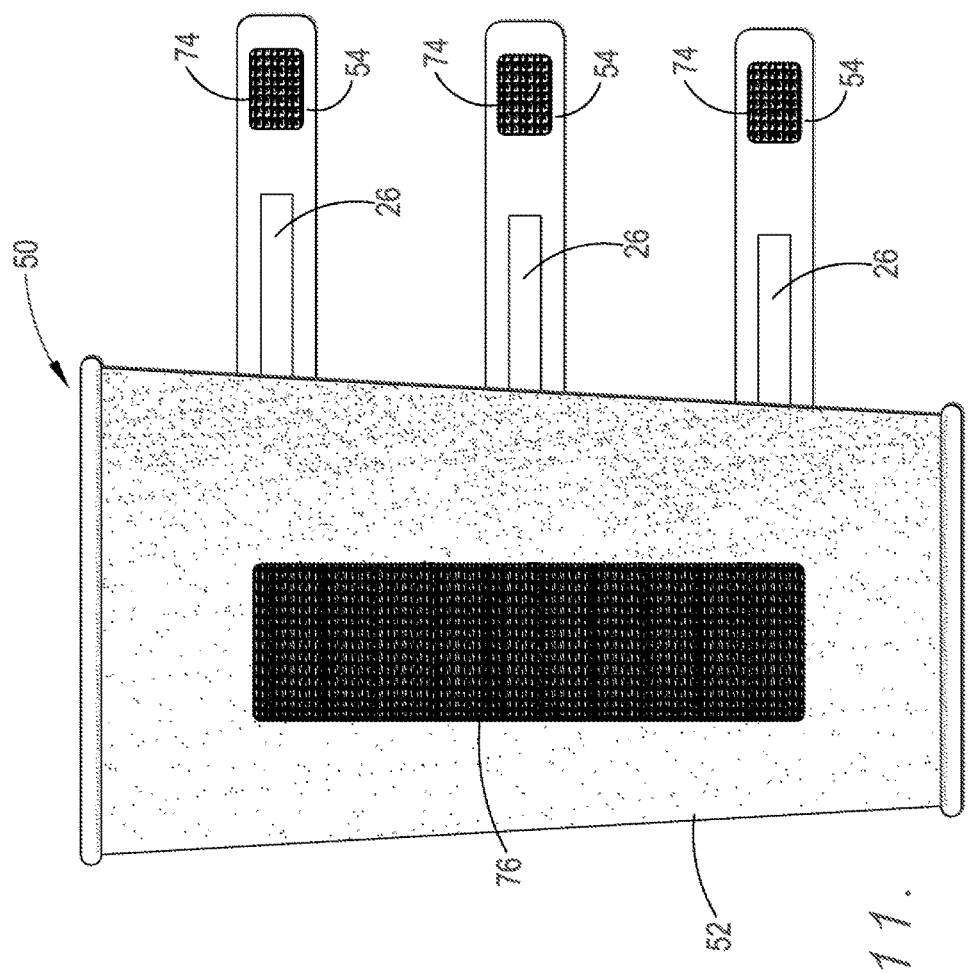
FIG. 11 is a right side elevational view of the pressure device from FIG. 10.

As illustrated in FIGS. 9 and 11, each of the pressure straps 54 contains a pocket 56, 56a that is integral with the strap. In certain embodiments, as illustrated in FIGS. 18-19, the pockets 56, 56a located on adjacent straps 52 are separated from each other by a distance 62. In certain embodiments, as best illustrated in FIGS. 18-19, an elongated pressure member 64, 64a is contained within each of the pockets 56, 56a. During use of the pressure device 50 in certain embodiments, the pressure members 64, 64a are oriented substantially perpendicular to a longitudinal axis of the limb and each pressure member creates a distinct line of pressure across the muscles and/or bone of the limb. Each element is discussed in more detail below.

In certain embodiments of the present invention, the pressure device 50 includes only the sleeve 52 without any straps 54. In some embodiments, such as illustrated in the drawings, the sleeve 52 of the pressure device 50 is formed in a shape of a hollow frustoconical. Thus, a material forming the sleeve 52 has an interior surface and an exterior surface. In the embodiments in which the sleeve 52 is frustoconical, an inner diameter of the sleeve is generally greater at an upper portion of the sleeve than at a lower portion of the sleeve. Embodiments provide for the inner diameter to be sufficient for the sleeve 52 to fit around the limb (i.e., an arm or a leg) of a human, such as illustrated in FIG. 5. Thus, it is understood that the material forming the sleeve 52 may, in some embodiments, be elastic and capable of stretching or expanding over a user's limb. In some embodiments, the inner diameter at the upper portion of the sleeve 52, when not in use on a user's limb, will be between about 3 inches to about 5 inches. In addition, the inner diameter at the lower portion of the sleeve 52 will be between about 2 inches to about 4 inches. Between the upper portion to the lower portion, the inner diameter of the sleeve 52 will vary continuously from a largest magnitude (i.e., at the upper portion of the sleeve) to a least magnitude (i.e., at the lower portion of the sleeve). In some other embodiments, the sleeve 52 of the pressure device 50 is formed in a shape of a hollow cylinder. In such embodiments, the inner diameter of the sleeve is generally the same along an entire longitudinal length of the sleeve (i.e., from the upper portion of the sleeve to the lower portion of the sleeve). For instance, in some embodiments, the inner diameter will be between about 2.5 inches to about 5 inches along the entire length of the sleeve 52.

Certain embodiments of the present invention, as illustrated in FIGS. 6-9, provide for the sleeve 52 to include two or more openings 66 formed through the thickness of the sleeve near, or at, the sleeve's upper portion. In some embodiments, such as that shown in FIGS. 6-9, there are two openings located diametrically opposite each other. The openings 66 will have various sizes and shapes. In some embodiments, the openings will be of sufficient size so as to accept one or more fingers of a user of the pressure device 50. As will be discussed in more detail below, the openings 66 facilitate the pressure device 50 being placed on user's limb by allowing the user to insert the user's fingers within the openings and pull the pressure device onto the user's limb. In other embodiments, such as shown in FIGS. 10-11, the sleeve 52 includes no such openings 66.

The pressure device 50, including the sleeve 52, in some embodiments is constructed of a suitable flexible material such as woven fabric, neoprene, spandex, nylon, other polyamides, or combinations thereof, as described above. In certain embodiments, the material will be perforated (i.e., breathable) to increase permeability and breathability. In some other embodiments, the material utilized to construct the pressure device 50 will have some elastic qualities, or in other embodiments, the material is mostly inelastic. If elastic materials are utilized, the inner diameter of the sleeve 52 may be significantly smaller than the limb, such that the sleeve is operable to expand over the limb when in use. In certain embodiments, the pressure device 50 is mostly made of a single material for ease of manufacture or, in alternative embodiments; it is made from a combination of materials where the materials are chosen for specific purposes. For example in some embodiments, one portion of the pressure device 50 is formed from relatively inelastic fabric while another portion is formed from somewhat elastic neoprene. In certain embodiments, a portion or multiple portions of the pressure device 50 are formed of solid materials (e.g., thin polymer sheets) to add strength to the device or to focus pressure in a particular area. In some embodiments, the material of the pressure device 50 includes multiple layers that are laminated together. For example, the pressure device 50 will, in some embodiments, will be formed form a single first layer of material that includes a second layer of material laminated over both the interior and exterior sides of the first material.

In certain embodiments, such as illustrated in FIGS. 6-9, the pressure device 50 includes a second material 68 that is secured to the exterior surface of the sleeve 52. In certain embodiments, the second material 68 is formed from a material that is different from that material of which the sleeve 52 is formed. The second material 68 will be formed, in some embodiments, from a breathable, dry-fit material such as a perforated neoprene, perforated polyamide, or the like that is thinner, lighter, and more breathable than the material of which the sleeve 52 is formed. In some embodiments, the second material 68 is secured to the exterior surface of the sleeve 52, such that the second material is positioned between the sleeve 52 and the straps 54. In certain other embodiments, a portion of the sleeve 52 is cut-out and removed, and the second material 68 replaces the cutout portion. In such embodiments, the second material 68 is positioned between the straps 54 and a user's limb, during use of the pressure device 50. The second material 68 is capable of being secured to the sleeve 52 by various means of attachment, such as stitching (including double stitching), adhesive, or the like. In embodiments, in which the sleeve 52 has a frustoconical shape, the second material 68 will have a larger width near an upper portion of the sleeve and a smaller width near a lower portion of the sleeve. In certain embodiments, the second material 57 will have a, arcuate-shaped circumference. In such embodiments, the second material 68 will have larger widths near where the straps 54 are located and smaller widths between such larger widths. In other embodiments, such as illustrated in FIGS. 10-11, the sleeve will only be made from a single material, with such single material comprising either the first materials or the second materials described above.

As with the straps 12 discussed previously, the architecture of the plurality of straps 54 can vary considerably. In certain embodiments, the straps 54 are formed of a single layer of material, or in alternative embodiments, the straps 54 are made of multiple layers of material. If a single layer of material is used, slight adjustments in the manner of attaching the pressure members 64, 64a (discussed below) to the straps 54 are necessary. Such adjustments are well within the knowledge of those skilled in the art.

In some embodiments the straps 54 are formed of multiple layers as shown in FIGS. 12-19. The bands 54 shown in the figures comprises a first layer 70 attached to a second layer 72. In other embodiments, additional layers can be utilized if desired. For example, in some embodiments, a layer of foam is added to provide comfort for the user.

As illustrated by FIGS. 7-8 and 10, the straps 54 of the device 50 are secured to the sleeve 52 by securing the first end of each of the straps to the sleeve. In certain embedment's, the first ends of the straps 54 are secured to the sleeve 52 via stitching. In other embodiments, the first ends of the straps 54 will be secured via adhesive or the like.

As illustrated in FIGS. 9 and 11, the pressure device 50 includes adjustable cooperative fasteners proximate the second ends of each of the straps 54 and on the sleeve 52 for adjustably fastening the straps about the sleeve, to create compressive forces or pressures about the limb, and for adjusting the forces/pressures applied to the limb. In certain embodiments, such as illustrated in the figures, a Velcro type fastener is utilized. As illustrated in FIG. 9, a strip of hook portion 74 is located on the second ends of the straps 54, and a loop portion loop portion 76 is located on the exterior surface of the sleeve 52. Although Velcro type fasteners are preferred due to ease of use, in other embodiments, other types of fasteners such as buckles, snaps, latches, or the like can be used in the practice of the invention. For example, in certain embodiments, a metal or polymeric loop is attached to the sleeve 52, and the second end of the strap 54 is capable of being inserted through loop and secured in place with Velcro, prongs, clasps, or the like. In certain embodiments, such as those illustrated in FIG. 9, the fasteners located on the sleeve 52 include a plurality of individual loop portions 76 disposed on the sleeve. In other embodiments, such as illustrated in FIG. 11, the fasteners on the sleeve 52 include a single, extending loop portion 76 that traverses from near an upper portion of the sleeve to near the lower portion of the sleeve.

FIG. 5 illustrates the pressure device 50 positioned on a limb of a user, with the engagement of the fasteners 74, 76. With both ends of the straps 54 secured to the sleeve 52, the pressure device generates two different sources of pressure against the user's limb. A first source of pressure results from the sleeve 52. The sleeve 52, formed in some embodiments from elastic material, generates an area of pressure that compresses the muscle around the limb inward. In embodiments in which the device 50 is used to treat shin splints, the sleeve 52 is placed around the user's lower leg, including the user's calf muscle. As such, the sleeve 52 compresses the calf muscle inward. Furthermore, because a lower portion of a normal user's calf muscle does not extend away from the user's leg as an upper portion of the user's calf muscle, the sleeve 52 is operable to support and force the upper portion of the user's calf muscle upward. Additional benefits of providing area compression of the muscle are described in more detail below. The second source of compressive force is provided by the pressure device 50 is due to the individual straps 54. As the second ends of the straps 54 are secured to the sleeve 52, the straps tighten around the limb causing compressive forces to be applied to the limb due to the elongated pressure members 64, 64a within the pockets 56, 56a of the straps. Such forces are discussed in more detail below.

In one embodiment of the device 50 according to embodiments of the present invention, the means for applying the plurality of discrete lines of pressure to the limb include the plurality of pockets 56, 56a and the elongated pressure members 64, 64a that are integral to each of the straps 54. In certain embodiments, the pockets 56, 56a are formed within the straps 54, or in alternative embodiments, are formed separately and attached to the straps.

In certain embodiments, the manner in which the pockets 56, 56a are formed vary with the methods used to manufacture the pressure device 50. For example, in the embodiment of the invention shown in the figures, the straps 54 are formed of multiple layers of material. In such embodiments, the straps 54 are formed of the first layer 70 of material attached to a second layer 72 of material, as discussed above.

The method of attaching the first layer 70 to the second layer 72 includes any method known in the art such as sewing or gluing. Those skilled in the art can pick the method of attachment that is most suitable for the materials used to construct the pressure device 50.

In the embodiment shown in FIGS. 8-9, 12-13, 16, and 18, the first 70 and second 72 layers are joined by laminating the layers together. The pockets 56 are located intermediate the first and second layer 70, 72 in the potential space that exists between the layers. In certain embodiments, the pockets 56 are completely enclosed, or in other embodiments, they have small openings (not shown) at one end. Providing small openings allows the user to change out the pressure members 64, 64a (described in more detail below) that reside therein (e.g., remove a more rigid member for a more compliant member).

Turning now to FIGS. 10-11, 13-15, 17, and 19, in an alternative embodiment, the straps 54 are constructed such that the pockets 56a are primarily arranged to be on one side of the straps 54. As with the ebmoduments described above, the embodiments illustrated in FIGS. 10-11, 13-15, 17, and 19 include the first 70 and second 72 layers being joined by laminating the layers together. In both embodiments, and particularly the embodiment shown in FIGS. 10-11, 13-15, 17, and 19, the straps 54 can be described as having an inside surface 78 and an outside surface 80 where the inside surface 78 faces the limb when in use. As such, the pockets 56a are positioned primarily on the inside surface 78 of the straps 54. In some embodiments, the pockets 56a have small openings (not shown) that allow a user to replace and/or change-out pressure members.

The pockets 56a shown in FIGS. 10-11, 13-15, 17, and 19 are similar to the pockets shown in FIGS. 8-9, 12-13, 16, and 18 in that they are positioned intermediate a first 70 and second 72 layer. They are different in that the portion of the straps 54 that is between pressure members 64a and the outside surface 80 is reinforced to be more rigid and less capable of deforming to conform to the shape of the pressure member 64a as shown in FIGS. 10-11.

In some embodiments of the present invention, reinforcement of the straps 54 to form the style of pockets 56a shown in FIGS. 10-11, 13-15, 17, and 19 can take several forms. One option is to place a backing plate 82, such as shown in FIG. 19, intermediate the pressure members 64a and the outside surface 80. In certain embodiments, the backing plate 82 is semi-flexible (for example, a thin piece of plastic). In other embodiments, the backing plate 82 is formed from a rigid material that has a curvature to conform to the natural curvature of the limb. Another alternative embodiment for reinforcing the straps 54 is to use multiple layers of material (e.g., fabric, leather) to create the "outer" portion the straps. Either method of reinforcement, results in pockets 56a that generally protrude toward the inside of the straps 54.

The pressure members 64, 64a used in the practice of the invention are sized to fit within the pockets 56, 56a. The pressure members are elongated to provide continuous lines of pressure that extend for a distance across a muscle, muscle group, and/or bone of a limb. Those skilled in the art recognize that the pressure (and force vectors) applied by the pressure members 64, 64a to a limb extends along lines that are generally perpendicular to the longitudinal axis of the limb.

As with the pressure members described above with respect to the band 10, pressure members having a circular or hemispherical cross-section are preferred because they create a generally smooth and uniform force transfer surface (generally represented by numeral 84) when compressed against a limb. In other embodiments, other cross sections (for example, hexagonal or star shaped) are used in the practice of the invention and may provide more relief for some users. In addition, embodiments provide for the pressure members 64, 64a to be either solid or hollow as shown in FIGS. 18 and 19 respectively. Similarly, embodiments provide for the material used to construct the pressure members to vary depending upon the amount of pressure desired. For example, a hollow tube of very flexible and soft rubber would have a pressure distribution profile that is different from a solid tube of fairly rigid nylon. One user may prefer one type of pressure member over another.

In certain embodiments, each of the pressure members 64, 64a on the straps 54 will have similar lengths. For instance, in some specific embodiments, each of the pressure members 64, 64a will have a length within a range from about 2 inches to about 5 inches. In certain specific embodiments, each of the pressure members 64, 64a will have lengths that are about 3 inches, 3.5 inches, or 4 inches. In certain other embodiments, one or more of the pressure members 64, 64a of the straps 54 will have different lengths. For instance, in certain embodiments in which the pressure device 50 is positioned on a user's lower leg, the pressure members 64, 64a that are positioned higher on the pressure device 50 will be longer than the pressure members 64, 64a that are positioned lower on the pressure device 50. With reference to FIGS. 8 and 10, for example, the pressure members 64, 64a positioned near the upper portion of the pressure device 50 are longer than the pressure members 64, 64a positioned near a lower portion of the pressure member. Such embodiments may be beneficial for use on a user's leg because a width of the user's leg generally decreases moving from an upper portion of the leg to a lower portion of the leg. In certain embodiments in which the pressure members 64, 64a are of different lengths, a first pressure member that is positioned directly below a second pressure member will have a length that is about 95 percent, 90 percent, 85 percent, 80 percent, 75 percent, or less than the length of the second pressure member. In certain specific embodiments of the pressure device 50, such as illustrated in the drawings and that include three straps 54 and three pressure members 64, 64a, the band will include an upper pressure member that is about 4.00 inches long, a middle pressure member that is about 3.5 inches long, and a bottom pressure member that is about 3 inches long. However, it should be understood that embodiments may provide for pressure members of different lengths than those specifically described above. Furthermore, in certain embodiments, the straps 54 will also have different sizes, with the straps 54 on the upper portion of the device 50 being longer than those on the lower portion of the device.

As previously described, in certain embodiments, the pockets 56, 56a are separated from each other by a distance 62. The length of the distance 62 is that which is sufficient to create a plurality of separate and discrete lines of pressure. Stated alternatively, the pressure members 64,64a do not touch or adjoin or abut to create a single, concentrated, uniform area of pressure when the pressure device 50 is applied to a limb. Stated in yet a further alternative, the lines of force vectors created by the pressure members 64, 64a and which are directed toward the limb are separated by a distance that is greater than the sum of the radii of any two adjacent pressure members 64, 64a. Stated more simply, there is a gap between adjacent pressure members 64, 64a.

Embodiments of the present invention provide for the distance 62 between the pockets 56, 56a and pressure members to vary depending upon the size of the pressure members, the width of the straps 54, the pocket material thickness, and the size of the limb. For those pressure devices 50 used in the treatment of shin splints, embodiments provide for the distance 62 to range between about 1 inch to about 4 inches or greater. In other embodiments, the distance 62 ranges between about ¼ inch to about ¾ inch. In still other embodiments, the distance 62 ranges from about 3 inches to about 5 inches. Furthermore, it is envisioned that a certain distance 62 that provides relief for some users will not provide relief for other users. Thus, it is expected that pressure devices 50 of various sizes and distances 62 will be manufactured in accordance with the practice of the invention. Furthermore, although the distance 62 has been described above as referencing the distance between adjacent pockets 56, 56a, some embodiments provide for such distance to refer specifically to a distance between pressure members 64, 64a.

As described, embodiments of the present invention allow for the pressure members 64, 64a to apply discrete lines of pressure to muscle, tendon, and/or bone of a limb. In particular, the lengths of the pressure members 64, 64a (as described above) and the separation distance 62 between the pressure members (as described above), allow for the discrete lines of pressure to be applied to the limb in a plurality of arrangements. For example, in some embodiments, all of the pressure device's 50 pressure members 64, 64a will be applied only to the muscles or muscle group of the limb, only to the tendon of the limb, or only to the bone of the limb. In other embodiments, one or more of the pressure members 64, 64a will be applied to the muscles or muscle group of the limb, while one or more other of the pressure members will simultaneously be applied to the tendons that connect the muscle or muscle group to the bone of the limb. In still further embodiments, one or more of the pressure members 64, 64a will be applied to the muscles, muscle group, and/or tendon of the limb, while one or more other of the pressure members will simultaneously be applied to the bone of the limb. Such varying arrangements for the application of the pressure members 64, 64a are due, in part, to the placement, length, and separation of each of the pressure members of the pressure device 50 according to embodiments of the present invention.

In addition to the pressure device 50 described above, embodiments of the present invention include a method for making the pressure device. In more detail, the method includes an initial step of forming a sleeve from the material or materials previously described. The method additionally includes a step of forming a plurality of straps, with the straps including pockets for retaining elongated pressure members. In a next step, elongated pressure members are inserted within the pockets of the straps, and a first end of each of the straps is secured to an exterior surface of the sleeve. A next step of the method includes forming two or more openings on through a thickness of the material of the sleeve, with the opening positioned on an upper portion of the sleeve. In a final step, adjustable cooperative fastener components are secured to a second end of each of said straps and to said sleeve. In some embodiments of the present invention, additional steps will be included in the method. For instance, the method may include the step of attaching a second material to said material of the sleeve. Furthermore, the step of forming the sleeve will, in some embodiments, includes forming the sleeve in a frustoconical shape, such that a diameter of the upper portion of said sleeve is generally greater than a diameter of a lower portion of said sleeve.

Another aspect of the invention is a method of simultaneously applying both an area of compressive force and a plurality of discrete lines of pressure to the muscles and/or bone of a limb, such as a human leg. The method comprises the step of encircling a limb with a compressive sleeve such as the pressure device 50 with the compressive sleeve 52 discussed above. Next, the device utilized in the method has adjustable cooperative fastener components on second ends of the straps and on an exterior surface of the sleeve, for adjustably fastening the straps about the limb. The device also possesses a plurality of elongated pressure members, such as those described previously, where the pressure members are separated by a distance and oriented substantially perpendicular to the longitudinal axis of the limb when the device is in use. The pressure members are preferably retained within discrete pockets that are integral to the straps of the device as discussed previously.

The method continues by adjusting the cooperative fastener components for each of the straps to tighten the straps around a portion of the limb thereby compressing each pressure member against the limb to create discrete lines of pressure across the muscles and/or bone of the limb where the lines of pressure are separated by a distance. Because each of the straps includes its own pressure member, embodiments of the present invention provide for a user to independently adjust a magnitude of the pressure applied via each the pressure members. As such, the device of the present invention is capable of applying varying magnitudes of pressure for each of its straps and pressure members, such that a user can customize the applied lines of pressure as may be required for the user's individual needs. For example, if a user applies the device 50 of embodiments of the present invention to the user's shin to treat shin splints, the user can individually adjust the amount of pressure applied to the user's leg via each strap 54 and its included pressure member 64, 64a. In more detail, if an upper portion of the user's shin is more inflamed than a lower portion, the user can apply greater pressure to the upper portion than the lower portion. Specifically, the user can adjust the cooperative fastener components of the straps 54 so that upper straps are fastened tighter than lower straps. As such, the pressure members 64, 64a associated with the upper straps will impart greater pressures, than the pressure members associated with the lower straps. Furthermore, while the pressure members 64, 64a provide for discrete lines of pressure, the compressive sleeve 52 will provide an area of pressure around the user's limb, including in the case of treating shin splints, to the calf muscle to the back of the user's leg and the gastrocnemius, soleus, and plantar muscles to the front and side of the user's leg. The area of pressure will force the muscles in towards the leg and will also provide support and lift for the muscles. Such area of pressure (i.e., the compression) reduces the natural stress realized by the muscles, as well as provides for increased blood flow by allowing the arteries and veins within the legs to relax.

In yet another aspect, the invention is a method of simultaneously applying both an area of compressive force a plurality of discrete lines of pressure to the muscles and/or bone of a limb. The method comprises the initial step of encircling a limb with a compressive sleeve such as the pressure device 50 with the compressive sleeve 52 discussed above. The method further comprises placing a plurality of discrete elongated pressure members against a limb where the elongated pressure members are the same as those discussed in relation to the pressure device 50 according to the invention. When the device is in use, the elongated pressure members are substantially perpendicular to the longitudinal axis of the limb and are separated from each other by a distance. The pressure members also have a force transfer surface that extends for a distance across the surface of the limb.

The method continues with the step of creating a circumferential compressive force around the limb. This step is typically accomplished with the application of the compressive sleeve 52 and by tightening the straps 54 around the limb to create compressive forces, such as illustrated by in FIG. 5. Tightening the straps 54 of the device 50 forces the pressure members, more specifically the force transfer surfaces 84 of the pressure members 64, 64a into the limb, which concentrates a portion of the compressive force applied to the limb at the force transfer surface. This in turn creates the continuous lines of pressure that aid in dampening movement of the muscles, tendons, and/or bone.

In the drawings and specification, there have been disclosed typical embodiments on the invention and, although specific terms have been employed, they have been used in a generic and descriptive sense only and not for purposes of limitation, the scope of the invention being set forth in the following claims.

I claim:

1. A therapeutic pressure device for applying pressure to a shin of a user, said device comprising:
   a compression sleeve for encompassing the shin and for providing an area of compressive force around the shin during use;
   a plurality of flexible straps attached to said compression sleeve, each strap comprising:
      a first end fixedly secured to said sleeve;
      a second end comprising an adjustable cooperative fastener component for selectively securing said second end of said strap to said sleeve and for adjustably positioning said strap about the shin, thereby moving said strap from an unsecured configuration to a secured configuration; and
      an elongated pressure member positioned between said adjustable cooperative fastener component and said first end of said strap,
   wherein said straps are adapted to be oriented substantially perpendicular to a longitudinal axis of the shin during use, and whereby each pressure member is operable to create an independent magnitude of pressure across the shin.

2. The device of claim 1, wherein said compression sleeve includes two or more openings extending through a material of the sleeve, wherein the openings are operable to assist a user in applying the device to the shin.

3. The device of claim 1, wherein said compression sleeve is formed from a material comprising neoprene.

4. The device of claim 3, wherein said material comprising neoprene is a first material, and said sleeve further includes a second material secured to a portion of an exterior of said sleeve.

5. The device of claim 4, wherein said second material is secured to said first material such that said second material is positioned between said flexible straps and a user's shin during use of said device.

6. The device of claim 1, wherein said fastener components comprise hook and loop material.

7. The device of claim 1, wherein each of said straps includes a pocket and wherein each pocket retains at least one of said pressure members such that said pressure member is radially displaced from said adjustable cooperative fastener component when said strap is in the secured configuration.

8. The device of claim 7, wherein the portion of each of said strap having said pocket comprises a first layer attached to a second layer with said pocket formed between the first and second layer.

9. The device of claim 1, wherein adjacent pressure members are separated by a distance that is between 1 inch and 3 inches.

10. The device of claim 1, wherein said elongated pressure members are solid in cross-section.

11. The device of claim 1, wherein said elongated pressure members are hollow in cross-section.

12. The device of claim 1, wherein said compression sleeve has a cylindrical shape, such that a diameter of said sleeve is generally the same along a longitudinal length of said sleeve.

13. The device of claim 1, wherein said compression sleeve has a frustoconical shape, such that a diameter of an upper portion of said sleeve is generally greater than a diameter of a lower portion of said sleeve.

14. The device of claim 1, wherein each of said pressure members has a length, and the lengths of all of said pressure members are not equal.

15. The device of claim 14, wherein a first length of a first pressure member positioned below a second pressure member is less than a second length of the second pressure member, and wherein the first length is between 80 percent and 95 percent of the second length.

16. A method of forming a device for providing pressure to a shin the method comprising the steps of:
   forming a sleeve from a material comprising a perforated fabric;
   forming a plurality of straps, each strap including a pocket for retaining an elongated pressure member;
   securing a first end of each of said straps to an exterior surface of the sleeve;
   forming two or more openings through a thickness of the material of the sleeve, each opening positioned on an upper portion of the sleeve and being operable to receive one or more finger of a user, thereby facilitating pulling the device onto the shin;
   securing an adjustable cooperative fastener component to a respective second end of each of said straps, each said adjustable cooperative fastener component being configured to selectively secure said respective second end of said respective strap to said sleeve, thereby moving said respective strap from an unsecured configuration to a secured configuration about the shin; and
   inserting one of said elongated pressure members into a respective pocket of each of said straps such that each elongated pressure member is positioned between a respective adjustable cooperative fastener component and respective first end of said respective strap.

17. The method according to claim 16, further comprising the step of attaching a second material to said material comprising a perforated fabric, wherein said second material is positioned between said straps and the shin of a user during use.

18. The method according to claim 17, wherein the step of forming the sleeve includes forming the sleeve in a frustoconical shape, such that a diameter of the upper portion of said sleeve is generally greater than a diameter of a lower portion of said sleeve.

19. The method according to claim 16, wherein each of said pressure members has a length, and the lengths of all of said pressure members are not equal, such that a first length of a first pressure member positioned below a second pressure member is less than a second length of the second pressure member, and wherein the first length is between 80 percent and 95 percent of the second length.

20. The method according to claim 16, wherein each said elongated pressure member is radially displaced from said respective adjustable cooperative fastener component when said respective strap is in the secured configuration.

\* \* \* \* \*